Figure 1:
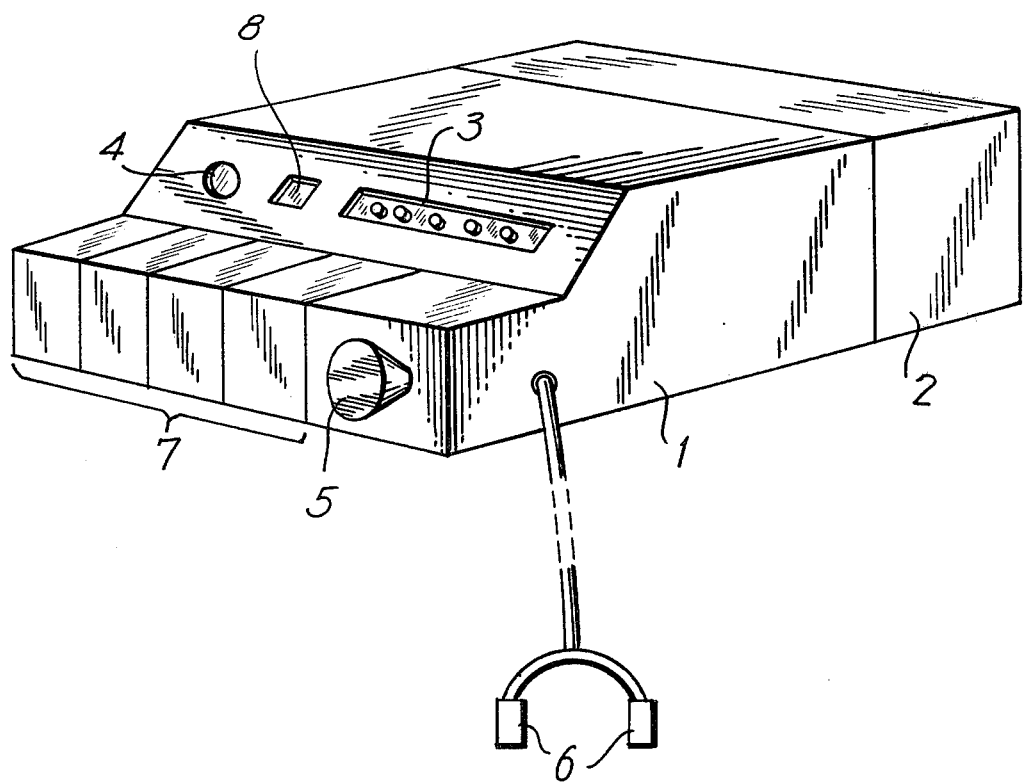

United States Patent [19]

Ágoston

[11] 4,184,485

[45] Jan. 22, 1980

[54] MEASURING ARRANGEMENT FOR DECREASING THE EMOTIONAL INFLUENCE ON INSTRUMENTAL DIAGNOSTICAL MEASUREMENTS

[75] Inventor: Mihály Ágoston, Budapest, Hungary

[73] Assignee: Medicor Müvek, Budapest, Hungary

[21] Appl. No.: 859,287

[22] Filed: Dec. 12, 1977

[30] Foreign Application Priority Data

Feb. 13, 1975 [HU] Hungary .................................. 1834

[51] Int. Cl.² .............................................. A61B 5/04
[52] U.S. Cl. .................................... 128/670; 128/905; 128/732
[58] Field of Search ........... 128/2.1 B, 2.1 M, 2.05 R, 128/2 R

[56] References Cited

U.S. PATENT DOCUMENTS

| | | | |
|---|---|---|---|
| 3,841,309 | 10/1974 | Salter et al. | 128/2.1 B |
| 3,855,998 | 12/1974 | Hidalgo-Briceno | 128/2.1 B |
| 3,880,144 | 4/1975 | Coursin et al. | 128/2.1 B |
| 3,882,850 | 5/1975 | Bailin et al. | 128/2.1 B |
| 3,924,606 | 12/1975 | Silva et al. | 128/2.1 B |
| 3,942,516 | 3/1976 | Glynn et al. | 128/2.1 B |
| 4,013,068 | 3/1977 | Settle et al. | 128/2.1 B |

*Primary Examiner*—Robert W. Michell
*Assistant Examiner*—Jeffrey W. Tayon

[57] ABSTRACT

Measuring arrangement for decreasing the emotional influence on instrumental diagnostical measurements, wherein the patient under test is encouraged to assume a rest condition by practicing the biological feed-back method, the operator observes the success of this activity on instruments, and the diagnostical measurements are performed when this instrumentally observed value falls within a predetermined domain that is characteristic of the rest condition. The arrangement comprises instruments for performing the diagnostical measurements, an EEG unit for providing biological feed-back, at least one further unit for conducting similar observations by biological feed-back on at least one of the temperature, pulse and skin conductivity of the patient, at least one operational mode switch, and an indicator unit to furnish information to both the patient and the operator about the value of the feed-back characteristic.

5 Claims, 2 Drawing Figures

MEASURING ARRANGEMENT FOR DECREASING THE EMOTIONAL INFLUENCE ON INSTRUMENTAL DIAGNOSTICAL MEASUREMENTS

This is a Divisional Application of the applicant's copending application Ser. No. 655,680, filed Feb. 6, 1976, titled "Method for Decreasing the Emotional Influence on Instrumental Diagnostical Measurements", now U.S. Pat. No. 4,126,125 dated Nov. 21, 1978.

In medical practice, in order to provide proper diagnoses, the results of instrumental tests obtained from the examined patient have an important role. Such instrumental diagnostical measurements are for example blood-pressure measurements, pulse measurements, electrocardiographic tests, measured values of body temperature, etc.

The results of the instrumental tests however depend not only on the momentary objective sick or healthy condition but also on the patient's excitedness, tiredness, that is his emotional condition. The phenomenon is for example well known according to which successive blood-pressure values obtained from the same patient have an asymptotically decreasing character. This evidently because any test being performed increases the excitedness and consequently the blood pressure of the patient, but he "gets used" to the test during the successive measurements, the excited condition gradually disappearing. The actual blood-pressure value is consequently not given by the first measurement.

The values of several other instrumentally determined characteristics are similarly influenced by the emotional condition of the patient, but with these a temporal course can be experienced that differs from blood-pressure measurements.

The existence of a direct correlation between the emotional condition and the instrumentally measured diagnostic characteristics is not questioned by any doctor; however so far there was no possibility for precisely exploring the correlation between the individual characteristics and the emotional condition, and this constitutes a "blank spot" in medical science.

When making the proper diagnosis the doctor has to make use of the experiences he has gained during his practice that may extend over decades, in order to be in a position correctly to evaluate any additional information obtained from the patient (anamnesis, physical tests, etc.). This method is inaccurate on account of its subjective nature and is additionally rather time consuming. With most tests there is insufficient time to develop a proper evaluation.

There are also cases where the instrumentally measured data that depart from the norms are not the results of organic irregularities or sicknesses but of neuroses of different degrees or of other psychic irregularities. A therapy directed to the reduction of the outstanding characteristics could lead to a misinterpretation of the actual sickness.

On the basis of the above, endeavors are justified in order to make objective the instrumental diagnostical tests but these endeavors did not produce so far any results.

In the psychiatric and neurological practice the biological feed-back method is widely used, on account of which serious therapeutic results have already been achieved.

It is the essence of this biological feed-back method that information is furnished to the person adopting the method, in a perceptible manner (by sound or light indication), about the physiological processes of his own organism, of which processes he does not become aware. On the basis of the furnished information, in a surprising manner, the human organism is capable of willingly controlling the fed-back processes which do not belong to direct intentional control. In the application of biofeedback the instrument plays an important role that receives, transforms the inner physiological processes or some accompanying phenomena thereof, and makes them accessible to natural sensory organs although they are otherwise inaccessible to them. In the biofeedback situations the appearance of the projected physiological processes is always sensory, in that the person under test, in one form or another, always sees or hears his own processes. The processing performance of the artificial organ that serves to receive, process and indicate the bioelectric process can however vary so that the same physiological process can be indicated in a senscry image of a varying abstraction level.

The most wide-spread application of biofeedback is attached to electroencephalography. It has been proven by tests that the dominant appearance of the alpha rhythm indicates an alert and relaxed condition, and a plurality of the persons tested is capable of carrying themselves into this alert, restful condition by the biofeedback of the existence of the alpha rhythm, namely by the application of a short, so-called autogenic training.

Biofeedback is also being used in respect of characteristics that differ from those of electroencephalography. Such characteristics are body temperature, pulse rate and electrical conductivity of the skin.

The number of publications dealing with biofeedback can be counted by several thousands. It is a common characteristic that the method is being used within the framework of psychotherapy, or merely as an interesting experimental possibility.

The progagation of the biofeedback method was accompaniedby the appearance on the market of several instruments designed for this purpose. The most characteristic representatives of such instruments are constituted by the products of the Bio-Scan Corporation, sold under the Types ALPHASCAN 200, 400 and 600. It is a common characteristic of the instruments that the test person is made aware of the apparition of the alpha waves, while several pre-adjusted or adjustable target functions can be produced for the test person. The instruments are however incapable of indicating even the EEC image.

It is an object of the invention to provide a measuring arrangement the use of which is capable of decreasing the emotional influence during instrumental diagnostic measurements, that is one which makes the above-mentioned measurements more objective.

The invention is based on the recognition that the changes of emotional effects do not influence the values of the test characteristics even if the tested person is being brought into the standard resting emotional condition, by practising the biofeedback method, and if all measurements are being performed in this quiescent condition.

The bringing of the tested persons into the rest condition naturally poses several problems but they do not influence the basic principle. If the method based on the feed-back of the alpha waves is unsuccessful (for example because the tested person is neurotic or has a particular EEG image), then the biofeedback method is used by way of a feed-back of other characteristics, the test person being brought to a condition characteristic of rest, depending on the fruitfulness of these characteristics, or we establlish his neurosis. The negative result consequently contains an important diagnostic information, namely that the measured outstanding or abnormal characteristic is not of an organic but of a psychic origin.

The measuring arrangement according to the invention contains the instruments necessary for performing the instrumental diagnostical examinations, for example an EKG tester, a blood-pressure tester, a pulse measuring instrument, a reaction-time measuring unit, etc. as well as the EEG unit necessary for performing the biofeedback, and at least one unit for performing a different type of biofeedback. The biofeedback units lead through an operational mode switch to an indicating apparatus which gives separate signals about the value of the feed-back characteristic to the tested person and to the doctor performing the test.

The instruments that belong to the measuring arrangement and the test units are preferably disposed in a common housing, in the form of a single complex measuring system.

A substantial difference exists between the measuring arrangement according to the invention and the hitherto known complex measuring systems in that it is suitable for at least two biofeedbacks, and during the practice of the biofeedback not only all the measuring and test instruments are in a condition ready for measurement but the instrument that has just been used for biofeedback (for example the pulse meter, the thermometer, the EEG unit) are also provided with a measuring output so that, for example, there is a possibility for an oscilloscopic observation of the entire EEG image during the alpha feed-back.

The invention cannot be considered as a single variant of the biofeedback method because its primary purpose is to obtain diagnostical information while the use of biofeedback fulfills merely an auxiliary role and its purpose is to bring the examined patient into a standard condition.

With the application of the inventive measuring arrangement the biofeedback, as a method, leaves the territory of psychiatry and neurology, where it has been used almost exclusively so far, and makes instrumental measurements more objective in the terrain of general medical diagnostics.

The measuring arrangement according to the invention can be used not only for making more objective the diagnostical measurements but it is also suitable for discovering the unknown correlations between the various examined functions and the emotional condition. Measurements can namely be performed not only in the standard rest condition but also in the course of the autogenic training that leads thereto, and the diagrammatic sketching of the corresponding values of the obtained emotional values and of the measured parameters can be the source of valuable information, the scientific importance of which cannot even be evaluated.

Figure 2:
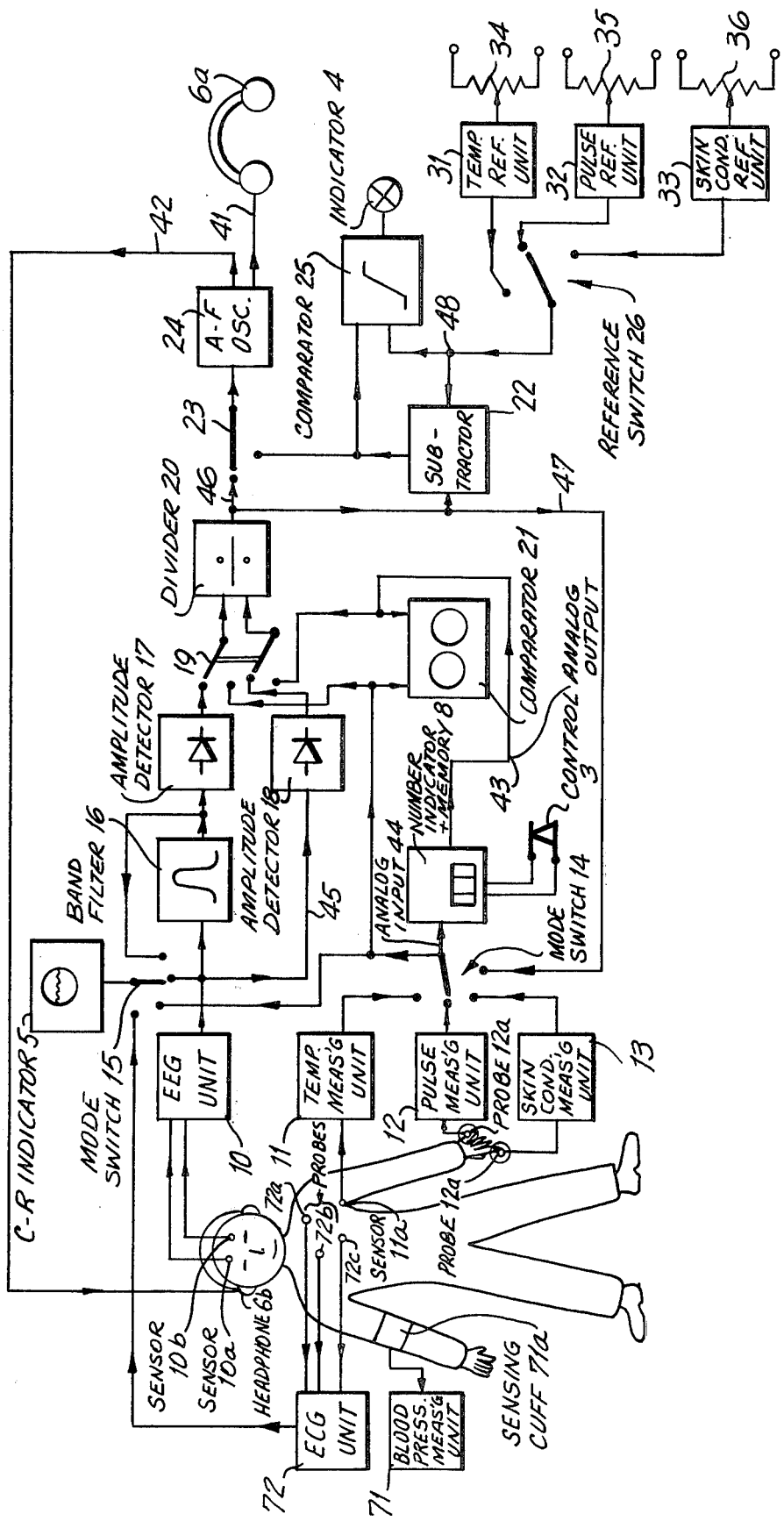

We describe the invention in the following in more detail on the basis of a practical example of the measuring arrangement, by reference to the drawings, wherein FIG. 1 is a perspective view of an instrument embodying the measuring arrangement according to the invention; and FIG. 2 is a functional block diagram of the measuring arrangement according to the invention.

In FIG. 1 we have shown an instrument containing the measuring arrangement according to the invention, having an apparatus housing 1 in which various measuring units 7 and the EEG and other units are lodged, the EEG unit serving for practicing the biofeedback. On the front panel of the instrument are located a cathode-ray (C-R) indicator 5 which displays the EEG and EKG images, an indicator lamp 4 which signals the successful termination of biodfeedback, control organs 3, and a number indicator 8 that has a memory therein. The electrodes, connecting and auxiliary devices required for performing the measurements and tests are lodged in an instrument casing 2 of the instrument. A headphone 6 for the test person can be plugged into a socket on the apparatus housing 1.

In FIG. 2 we have shown the functional block diagram of the measuring arrangement according to the invention, in which the tested person is schematically shown.

The following measuring units belong to the measuring arrangement: an EEG unit 10, a temperature measuring unit 11, a pulse measuring unit 12, a unit 13 for measuring skin conductivity, a blood-pressure measuring unit 71 and an EKG instrument 72.

The C-R indicator 5 can be connected to the appropriate test units by the aid of an oscilloscope operational mode switch 15 so that it displays their respective output signals. The measuring units are connected to the tested person by electrodes and sensors that are known per se. It can be seen in FIG. 2 that the patient (who, incidentally, may be male or female although this specification refers to the patient only as "he", for the sake of simpler identification) is connected for the tests with electrodes or sensors 10a, 10b that lead to the EEG unit, with a thermometer or the like sensor 11a that is connected to the input of the temperature measuring unit 11, with further sensors or probes 12a, 13a respectively feeding information to the pulse measuring and the skin conductivity measuring units 12 and 13. In a similar manner, a conventional sensing cuff 71a may be applied for operating the blood-pressure measuring unit 71, and/or appropriate sensors or probes 72a, 72b and/or 72c for the EKG instrument 72, attachable and usable independently or simultaneously. A switch 14 will be described somewhat later. The connection has been shown simultaneously for all measuring units, for the sake of a better illustration, this can however be developed in any sequence or coincidence.

The output of of the EEG unit 10 is connected to a band filter 16 which can be set, within a frequency band of 7 and 13 Hz, that is in the domain of the alpha waves, to various bandwidths and intermediate frequencies by using a non illustrated control organ. The characteristic bandwidth of the band filter 16 is 1 Hz, and consequently the entire domain can be covered in size bands. The output of the band filter 16 leads to an amplitude detector 17, the output of the latter presenting an analog signal that is proportional to the amplitude of the EEG components falling within the selected band.

The signal proportional to the overall EEG energy is furnished by an amplitude detector 18 which is directly controlled by the output of the EEG unit 10. It can be seen that the detector 18 is fed from the EEG unit 10 by way of a line identified by numeral 45. In the respective positions of the oscilloscope operational mode switch 15, the overall and the filtered EEG can also be directly observed. The outputs of the amplitude detectors 17 and 18 are fed to respective inputs of a divider circuit 20, namely in a first position of a switch 19 (corresponding to the EEG operational mode), whereby an analog signal is produced at the output of the divider circuit 20 which is proportional to the relative amplitude of the alpha waves.

This analog signal leads, on the one hand, through a switch 23 (in its first operational mode) to the control input of an audio-frequency oscillator 24 having an adjustable frequency while, on the other hand, it leads, through a line 47, to an output for the EEG mode of an operational mode switch 14. The common contact or wiper of the switch 14 is connected to the input of the indicator and memory unit 8. The indicator and memory unit 8 has an analog input 44 and an analog output 43. The unit 8 displays the signal led to the analog input 44 in digital form. Upon pressing the control organ 3, the displayed value is being written into the memory of the unit 8, and the stored value appears at the analog output 43 in the form of an analog signal.

The output 46 of the divider circuit 20 is also in connection with a non-inverting input of a subtractive circuit 22. The inverting input of the subtractive circuit 22 is connected, through a line 48, with the common contact or wiper of a reference switch 26 and with the reference input of a comparator 25. The control input of the comparator 25 connects to the output of the subtractive circuit 22. In the second operational mode of the switch 23, this output leads to the control input of the audio-frequency oscillator 24.

The output of the comparator 25 controls the indicator lamp 4. The reference switch 26 has three positions; in the individual positions, it is connected with reference units 31, 32 and 33 that serve for setting respective reference levels for the comparator 25, each corresponding to a predetermined value on the biofeedback units serving for the temperature probe 11, the pulse meter 12 and the skin conductivity tester 13, respectively. Level adjustment of the reference units is preformed with potentiometers 34, 35 and 36.

The output and the input of the indicator and memory unit 8 lead to the inputs of a second comparator 21, which comparator includes two signal lamps that are illuminated depending on which of the two inputs has a higher analog signal. The operator can thus immediately determine, on account of the lamps, whether the signal stored in the indicator and memory unit 8 is higher or lower than the signal led to the analog input 44.

The audio-frequency oscillator 24 has two headphone connections identified by numerals 41 and 42, one for a headphone 6b of the tested person, and the other for a headphone 6a of the doctor who conducts the test. It should be understood that in FIG. 1, these two headphones are identified in a simplified manner by the earlier-mentioned (single) headphone 6.

It will be understood by those skilled in the art that EKG and EEG are respective, widely accepted designations of electrocardiograms and electroencephalograms, respectively.

The operation of the measuring arrangement according to the invention is as follows. At the beginning of the instrumental diagnostical test, the required sensors are attached to the person being tested, and we place the headphone 6b on his head. The switches 19 and 23 are set to the first position, corresponding to EEG (the position illustrated in the drawing), and the operational mode switch 14 also in the EEG position, whereupon the line 47 connects to the input of the indicator and memory unit 8. Upon having adjusted the band filter 16, an analog signal appears at the output of the divider circuit 20, that corresponds to the relative amplitude of the alpha waves. This signal appears in digital form on the display of the indicator and memory unit 8, and determines the momentary frequency of the audio-frequency oscillator 24. Let us assume that increasing alpha activity is accompanied by decreasing tone pitch. We now tell the person being tested to try to reach a condition of rest, the success of which is indicated to him by the tone becoming deeper in his headphone 6b.

The doctor can observe the entire EEG wave and the alpha wave on the C-R display 5 by bringing the switch 15 into the appropriate position, and can hear the feedback tone in the headphone 6a, and he can also read the relative amplitude of the alpha waves in digital form from the display.

As soon as the tested person has reached a restful condition, the treating doctor can record the values measured from the instruments 71, 72 and from the units 10 to 13. It is important to note that the EEG unit 10 itself is no exception to the measurement, and its output can draw an EEG image, in the rest condition, by means of a not illustrated recording mechanism. With an alternative solution (not shown) the C-R display 5 can be photographed in the EEG position.

It is evident that it is immaterial from the standpoint of the invention what test instruments are being used and what measurements are being performed with them. It is however important that the value of the measured function be dependent upon the emotional condition.

The fact of the rest condition can be linked to a given alpha activity. There is also the possibility to increase the number of the reference units by one, and to form a not shown EEG position on the reference switch 26. In this case the given alpha activity can be signalled by the lamp 4 being lit, in addition to the digital number being visible on the display.

If it was not possible to bring the tested person into the prescribed rest condition by means of the autogenic training, then we switch the switches 19 and 23 into the positions corresponding to the second operational mode while one of the units 11, 12, 13 can be linked to the input of the indicator and memory unit 8 by way of the operational mode switch 14.

Let us assume that it is the pulse measuring unit 12 that is in the activated condition in this second operational mode. At the beginning of the test we actuate the control organ 3, and thus we store in the memory the initial pulse value. This value immediately appears at the analog output 43 in the form of an analog signal. We now invite the tested person to try, as a matter of example, to reduce his pulse rate. If now the pulse drops, then the output signal of the divider circuit 20 also drops, considering that it indicates the quotient of the momentary and the initial pulse values. The inverting input of the subtractive circuit 22 receives a reference signal that was preset with the potentiometer 35, but the signal level drops at the non-inverting input. In this case the control voltage of the audio-frequency oscillator 24 also drops, and the tone audible in the headphone 6b becomes higher. The tested person learns about the reduction of his pulse, on the one hand, by noticing the increase in the tone pitch, and, on the other, by seeing the momentary pulse number on the dial of the indicator and memory unit 8. The test is terminated when the control signal at the inputs of the comparator 25 coincides with the reference signal, and the lamp 4 turns on. The instrumental diagnostical measurements can now be preformed.

The measurement can also be continued by switching back to the EEG operational mode and observing the alpha activity. According to practical experience a patient can be brought much easier into the rest condition after a different intermediate biofeedback.

The most recommendable biofeedback method for a given case can be selected from among the units 11 ... 13 in accordance with the operator's experience. There are furthermore cases where it is not possible to bring the tested person into the rest condition. In this event we have indication, in the already mentioned manner, that the examined person is neurotic, and is unsuitable for an objective test.

With measuring arrangement according to the invention it is of course possible to take multi-variable functions from the various measured characteristics, the relative amplitude of the alpha waves, or the degree of the relative deviation, in the event of tests with the second operational mode.

Experience has shown that for pulse-rate measurements, when using the biofeedback method, it is recommended to prescribe a fluctuation of ±30%, constituting the dependent variable, and for temperature measurements one of max. ±10%. The potentiometers 34–36 consequently have to be made adjustable within these ranges.

The invention is of course not limited to the arrangement disclosed in connection with the example, since the individual switches and circuits can be substituted by others. The acoustic feed-back can thus be substituted, for example, by an optical feed-back, and the test units can be connected in the widest selection and chronological sequence.

I claim:

1. A measuring arrangement for decreasing the emotional influence on instrumental diagnostical measurements, comprising, in combination: instruments (7, 71, 72) for performing diagnostical tests on a patient; an EEG unit (10) for performing biofeedback; and at least one further unit, from among temperature, pulse and skin-conductivity measuring units (11, 12, 13), also for performing biofeedback; probes and sensors (10a, 10b, 11a, 12a, 13a, 71a, 72a, 72b, 72c) for hooking up the patient to respective inputs of said instruments, said EEG unit and said at least one further measuring unit; said units being linked to indicator means (5, 8) through an operational mode switch (14) having positions for at least a first, EEG mode and a second, different operational mode; said indicator means including means (6a, 6b) for furnishing separate information, to at least one of the patient and an operator, about the value of the feedback characteristics; wherein said EEG unit has an output that leads (45) to first (18) and second (17) amplitude detectors, the latter through a band filter (16) which has a switchable frequency band of between 7 and 14 Hz; said detectors have outputs connectable to respective inputs of a divider circuit (20) through a first switch (19), the latter also having positions for at least the first and the second operational modes; said divider circuit having an output (46) that furnishes a signal in the first mode that is proportional to the relative amplitude of alpha waves of the patient; said information furnishing means being constituted by at least one headphone operatively associated with a first one (42) of two outputs (42, 41) of an adjustable audio oscillator (24); a control input of the latter is selectively connectable in the first mode to said divider output through a second switch (23) also having positions for at least the first and the second operational modes; said indicator means including a combined display and memory unit (8), for displaying in the form of a digital number a signal, applied to an analog input (44) of said combined unit, and for storing the number upon actuation of a control member (3), while said combined unit furnishes the stored number at an analog output (43) thereof; said analog input is connectable (47) in the first mode to said divider output, and in the second mode to one of the respective outputs of said further measuring units; said analog input and said analog output are linked in the second mode to said respective divider inputs, to produce at said divider output the ratio of the instantaneous value of the analog signal and of the stored number, expressing the efficiency of the biofeedback; said divider output is connectable to one of the inputs of a subtractive circuit (22); an inverting-type input (48) of the latter is connectable to one of respective terminals of at least one reference unit (31, 32, 33), corresponding in number to that of said at least one further measuring unit; an output of said subtractive circuit is connectable in the second mode to said oscillator control input; and control means (15, 26) for selectively individually and simultaneously performing the aforesaid selective connections between said instruments, said EEG unit, said at least one further measuring unit, said indicator means, said detectors, said divider circuit, said oscillator, said combined unit, said subtractive circuit and said reference units, in association with said operational mode switch as well as said first and said second switches.

2. The measuring arrangement as defined in claim 1, wherein said control means (15, 26) includes a second operational mode switch (15) linked to the input of said indicator means (5) and having a number of positions that are selectable independently of the positions of at least said first-named operational mode switch (14).

3. The measuring arrangement as defined in claim 1, further comprising a first comparator (25); and wherein said terminals of the reference units (31, 32, 33), serving to indicate when a predetermined threshold level is attained, and said subtractive output (of 22) are both linked to respective inputs of said first comparator; and an output of the latter has associated therewith a display element such as an indicator lamp (4).

4. The measuring arrangement as defined in claim 1, further comprising a second comparator (21); and wherein said analog output (43) and said analog input (44) are connectable, in the second mode, and at least partly by said control means (15, 26), to respective inputs of said second comparator; and two outputs of the latter are associated with respective signal lamps that indicate which of said two inputs has a higher analog signal.

5. The measuring arrangement as defined in claim 1, wherein said control means (15, 26) includes a reference switch (26) between said inverting-type input (48) of the subtractive circuit (22) and said terminals of the reference units (31, 32, 33), with at least as many positions as there are reference units, the positions being selectable independently of the positions of at least one of said operational mode switch (14), said first (19) and said second (23) switches.

* * * * *